US006468775B1

(12) United States Patent
Ankenbauer et al.

(10) Patent No.: US 6,468,775 B1
(45) Date of Patent: Oct. 22, 2002

(54) THERMOSTABLE DNA POLYMERASE FROM CARBOXYDOTHERMUS HYDROGENOFORMANS

(75) Inventors: Waltraud Ankenbauer, Penzberg; Ursula Markau, Polling; Vitaly Svetlichny, Bayreuth; Gudrun Schmitz-Agheguian, Bernried; Astrid Reiser, Antdorf; Bernhard Angerer, Rosenheim; Christine Ebenbichler, Antdorf; Frank Laue, Paehl-Fischen, all of (DE); Elizaveta Bonch-Osmolovskaya, Moscow (RU)

(73) Assignee: Roche Molecular Systems Inc., Alameda, CA (US)

( * ) Notice: Subject to any disclaimer, the term of this patent is extended or adjusted under 35 U.S.C. 154(b) by 0 days.

(21) Appl. No.: 09/269,861

(22) PCT Filed: Oct. 1, 1997

(86) PCT No.: PCT/EP97/05391

§ 371 (c)(1),
(2), (4) Date: Nov. 22, 1999

(87) PCT Pub. No.: WO98/14589

PCT Pub. Date: Apr. 9, 1998

(30) Foreign Application Priority Data

Oct. 3, 1996 (EP) ............................................. 96115873

(51) Int. Cl.$^7$ .......................... C12N 9/12; C12N 15/00; C07H 21/04

(52) U.S. Cl. .................... 435/194; 435/183; 435/320.1; 435/252.1; 435/252.3; 435/325; 435/252.33; 536/23.1; 536/23.2; 530/350

(58) Field of Search ................................. 435/194, 195, 435/370.1, 252.33, 252.1, 252.3, 325; 536/23.2, 23.1; 530/350

(56) References Cited

U.S. PATENT DOCUMENTS 4,683,202 A  7/1987  Mullis ........................ 435/91

OTHER PUBLICATIONS

Beckman et al., "On the Fidelity of DNA Replication: Manganese Mutagenesis in Vitro", *Biochemistry*, 1985, 24: 5810–5817.
Bonch–Osmolovskaya and Stetter, "Interspecies Hydrogen Transfer in Cocultures of Thermophilic Archaea", *System. Appl. Microbiology*, 1991, 14: 205–208.
Braithwaite and Ito, "Compilation, alignment, and phylogenetic relationships of DNA Polymerases", *Nucleic Acids Research*, 1993, 21: 787–802.
Brinkmann et al., "High–level expression of recombinant genes in *Escherichia coli* is dependent on the availability of the dnaY gene product", *Gene*, 1989, 85: 109–114.

Brock et al., "*Thermus aquaticus* gen. n. and sp. n., a Non–sporulating Extreme Thermophile", *Journal of Bacteriology*, 1969, 98: 289–297.
Engelke et al., Purification of *Thermus aquaticus* DNA Polymerase Expressed in *Escherichia coli*, *Analytical Biochemistry*, 1990, 191: 396–400.
Höltke et al., "Sensitive Chemiluminescent Detection of Digoxigenin–Labeled Nucleic Acids: A Fast and Simple Protocol and Its Applications", *Biotechniques*, 1992, 12: 104–113.
Kaledin et al., "Isolation and Properties of DNA Polymerase from the Extremely Thermophilic Bacterium *Thermus ruber*", *Biochemistry* (translated from Russian), 1983, 47: 1515–1521.
Kaledin et al., "Isolation and Properties of DNA Polymerase from the Extremely Thermophilic Bacterium *Thermus flavus*", *Biochemistry* (translated from Russian), 1982, 46: 1247–1254.
Kornberg and Baker, *DNA Replication*, W.H. Freemann & Company, New York, 1992, pp. 130–132.
Lawyer et al., "Isolation, Characterization and Expression in *Escherichia coli* of the DNA Polymerase Gene from *Thermus aquaticus*" *The Journal of Biological Chemistry*, 1989, 264: 6427–6437.
Lundberg et al., "High–fidelity amplification using a thermostable DNA polymerase isolated from *Pyrococcus furiosus*", *Gene*, 1991, 108: 1–6.
Neuner et al., "*Thermococcus litoralis* sp. nov.: A new species of extremely thermophilic marine archaebacteria", *Archives of Microbiology*, 1990, 153: 205–207.
Ochman et al., "Amplification of Flanking Sequences by Inverse PCR", *PCR Protocols: A Guide to Methods and Applications*, 1990, pp. 219–227.
Perler et al., "Thermostable DNA Polymerases", *Advances in Protein Chemistry*, 1996, 48: 377–435.
Perler et al., "Intervening sequences in an Archaea DNA polymerase gene", *Proceedings of National Academy of Science USA*, 1992, 89: 5577–5581.
Raleigh et al., "McrA and McrB restriction phenotypes of some *E. coli* strains and implications for gene cloning", *Nucleic Acids Research*, 1988, 16: 1563–1575.
Ricchetti and Buc, "*E. coli* DNA polymerase I as a reverse transcriptase", *The EMBO Journal*, 1993, 12: 387–396.
Rosenberg et al., "Vectors for selective expression of cloned DNAs by T7 RNA polymerase", *Gene*, 1987, 56: 125–135.

(List continued on next page.)

Primary Examiner—Rebecca E. Prouty
Assistant Examiner—Richard G Hutson
(74) Attorney, Agent, or Firm—Pennie & Edmonds LLP

(57) ABSTRACT

A DNA polymerase from a thermophilic eubacterium is provided. The DNA polymerase shows magnesium ion dependent reverse transcriptase activity and 3'-5' exonuclease activity. The invention also includes recombinant plasmids and transformed host cells capable of producing the enzyme. The enzyme is classified into class EC 2.7.7.7., a DNA nucleotidyl transferase DNA-directed type.

8 Claims, 12 Drawing Sheets

OTHER PUBLICATIONS

Rüttimann et al., "DNA polymerases from the extremely thermophilic bacterium *Thermus thermophilus* HB–8", *Eur. Journal of Biochemistry*, 1985, 149: 41–46.

Spanos and Hübscher, "Recovery of Functional Proteins in Sodium Dodecyl Sulfate Gels", *Methods in Enzymology*, 1983, 91: 263–277.

Stüber et al., "System for High–Level Production in *Escherichia coli* and Rapid Purification of Recombinant Proteins: Application to Epitope Mapping, Preparation of Antibodies, and Structure–Function Analysis", *Immunological Methods*, 1990, pp. 121–152.

Studier et al., "Use of T7 RNA Polymerase to Direct Expression of Cloned Genes", *Methods in Enzymology*, 1990, 185: 60–89.

Svetlichny et al., "*Carboxydothermus hydrogenoformans* gen. nov., sp. nov., a CO–utilizing Thermophilic Anaerobic Bacterium from Hydrothermal Environments of Kunashir Island", *System. Appl. Microbiology*, 1991, 14: 254–260.

Triglia et al., "A procedure for in vitro amplification of DNA segments that lie outside the boundaries of known sequences", *Nucleic Acids Research*, 1988, 16: 8186.

1. E.COLI POL I (20U) + KLENOW FRAGMENT (10U)
2. CELL EXTRACT FROM C. HYDROGENOFORMANS (2μl)
3. CHY POLYMERASE, REC. (7U)
4. TAQ POLYMERASE (20U)
5. CELL EXTRACT FROM C. HYDROGENOFORMANS (2μl)
6. CHY POLYMERASE, REC. (14U)
7. E.COLI POL I (20U) + KLENOW FRAGMENT (5U)
8. CELL EXTRACT FROM C. HYDROGENOFORMANS (4μl)
9. CHY POLYMERASE, REC. (70U)
10. TAQ POLYMERASE (20U)

SEQ ID No.: 7

| | | | | | | | | | | | | |
|---|---|---|---|---|---|---|---|---|---|---|---|---|
| ATG | GGA | AAA | GTA | GTC | CTG | GTG | GAT | GGA | AAT | AGT | TTA | TTA | CAT | AGA | GCG | 48 |
| M | G | K | V | V | L | V | D | G | N | S | L | L | H | R | A | 16 |
| TTT | TTT | GCC | CTT | CCG | CTT | TTA | ACC | AAA | ACT | ACT | AAA | GGA | GAG | CCT | ACC | GGG | 96 |
| F | F | A | L | P | L | L | T | K | T | T | K | G | E | P | T | G | 32 |
| GCG | GTT | TAC | GGG | TTT | TTA | ACG | ATG | CTT | TTT | CGG | GTA | ATA | AAA | GAT | GAA | 144 |
| A | V | Y | G | F | L | T | M | L | F | R | V | I | K | D | E | 48 |
| AAA | CCC | GAA | TAT | TTA | GCG | GTA | GCT | TTT | GAT | ATT | AGC | CGG | AAA | ACT | TTT | 192 |
| K | P | E | Y | L | A | V | A | F | D | I | S | R | K | T | F | 64 |
| CGT | ACC | GAG | CAG | TTT | ACT | GCA | TAC | AAA | GGG | CAC | CGC | AAA | GAA | GCC | CCG | 240 |
| R | T | E | Q | F | T | A | Y | K | G | H | R | K | E | A | P | 80 |
| GAT | GAG | CTT | GTA | CCC | CAG | TTT | GCC | CTG | GTG | CGG | GAA | GTA | TTA | AAG | GTT | 288 |
| D | E | L | V | P | Q | F | A | L | V | R | E | V | L | K | V | 96 |
| TTA | AAT | GTT | CCC | TAT | ATT | GAA | CTT | GAC | GGT | TAT | GAG | GCC | GAT | GAT | ATT | 336 |
| L | N | V | P | Y | I | E | L | D | G | Y | E | A | D | D | I | 112 |

*Fig. 5.1*

| ATC | GGC | CAC | CTA | TCA | AGG | GCT | TTT | GCG | GGA | CAA | GGA | CAT | GAA | GTG | GTG | 384 |
| I | G | H | L | S | R | A | F | A | G | Q | G | H | E | V | V | 128 |
| ATT | TAT | ACC | GCT | GAC | CGG | GAC | ATG | CAA | CTG | GTA | GAT | GAA | AAA | ACG | 432 |
| I | Y | T | A | D | R | D | M | Q | L | V | D | E | K | T | 144 |
| GTG | GTA | TAC | CTT | ACC | AAA | AAA | GGC | ATT | ACC | GAA | CTG | GTT | AAA | ATG | GAT | 480 |
| V | V | Y | L | T | K | K | G | I | T | E | L | V | K | M | D | 160 |
| TTA | GCT | GCG | ATT | TTA | GAA | TAC | GGC | TTA | AAG | CCT | AAA | CAG | CTT | GTG | 528 |
| L | A | A | I | L | E | Y | G | L | K | P | K | Q | L | V | 176 |
| GAT | GTT | AAA | GGA | TTA | ATG | GGA | GAT | CCC | TCG | GAT | CCC | GGG | GTT | 576 |
| D | V | K | G | L | M | G | D | P | S | D | P | G | V | 192 |
| CCC | GGG | ATT | GGG | GAG | AAA | ACT | GCT | TTA | GAT | TTA | ATT | AAA | ACT | TAT | GGC | 624 |
| P | G | I | G | E | K | T | A | L | D | L | I | K | T | Y | G | 208 |
| TCA | GTG | GAA | GAA | GTT | TTG | GCC | CGT | AAA | GAT | GAG | TTA | AAA | CCT | AAA | TTA | 672 |
| S | V | E | E | V | L | A | R | K | D | E | L | K | P | K | L | 224 |
| AGA | GAA | AAG | CTT | GCC | GAA | CAC | GAA | AAT | TTA | GCA | AAA | ATA | TCG | AAA | CAA | 720 |
| R | E | K | L | A | E | H | E | N | L | A | K | I | S | K | Q | 240 |

Fig. 5.2

```
TTA GCT ACA ATC CTG CGG GAA ATA CCG TTA GAA ATC TCC CTG GAA GAT    768
 L   A   T   I   L   R   E   I   P   L   E   I   S   L   E   D    256
TTA AAA GTT AAA GAA CCT AAT TAT GAA CCT TTA GTT GCT AAA TTA TTT CTT    816
 L   K   V   K   E   P   N   Y   E   P   L   V   A   K   L   F   L    272
CAC CTT GAG TTT AAA AGC TTT TTA AAA GAA ATA GAA CCA AAA ATA AAG    864
 H   L   E   F   K   S   F   L   K   E   I   E   P   K   I   K    288
AAA GAA TAC CAG GAA GGT AAA GAT TTG GTG CAA GTT GAA ACT GTA GAA    912
 K   E   Y   Q   E   G   K   D   L   V   Q   V   E   T   V   E    304
ACG GAA ATT GCA CAG GTA GTT TTT AGT GAT GGA TTT TAT GTT GAT    960
 T   E   I   A   Q   V   V   F   S   D   G   F   Y   V   D    320
GAC GGG GAA AAA ACA AAG TTT TAC TCT TTA GAC CGG CTG AAT GAA ATA    1008
 D   G   E   K   T   K   F   Y   S   L   D   R   L   N   E   I    336
GAG GAA ATA TTT AGG AAT AAA AAA ATT ATT ACC GAC GAT GCC AAA GGA    1056
 E   E   I   F   R   N   K   K   I   I   T   D   D   A   K   G    352
ATT TAT CAT GTC TGT TTA GAA AAA GGT CTG ACT TTT CCC GAA GTT TGT    1104
 I   Y   H   V   C   L   E   K   G   L   T   F   P   E   V   C    368
```

Fig. 5.3

```
TTT GAT GCG CGG ATT GCA GCT TAT GTT TTA AAC CCG GCC GAC CAA AAT   1152
 F   D   A   R   I   A   A   Y   V   L   N   P   A   D   Q   N    384
CCC GGC CTC AAG GGG CTT TAT CTA AAG TAT CTA TTA CCG GTG TAT GAA   1200
 P   G   L   K   G   L   Y   L   K   Y   L   L   P   V   Y   E    400
GAT GTA TCT TTA AAC ATT AGA GGG TTG TTT TAT TTA AAA AAA GAA ATG   1248
 D   V   S   L   N   I   R   G   L   F   Y   L   K   K   E   M    416
ATG AGA AAA ATC TTT GAG CAG GAG CAA AGG ATG CAA TTT TAT GAA ATA   1296
 M   R   K   I   F   E   Q   E   Q   R   M   Q   F   Y   E   I    432
GAA CTT CCT TTA ACT CCA CTT GCT GTT CTT GCT CTT GAG CAT ACC ATT   1344
 E   L   P   L   T   P   L   A   V   L   A   L   E   H   T   I    448
CAG GTT GAC CGG GAA GCT TTA AAA GAA ATG TCG TTA GAG CTG GGA GAG   1392
 Q   V   D   R   E   A   L   K   E   M   S   L   E   L   G   E    464
CAA ATT GAA GAG TTA ATC CGG GAA ATT TAT GTG CTG GCG GGG GAA GAG   1440
 Q   I   E   E   L   I   R   E   I   Y   V   L   A   G   E   E    480
TTT AAC TTA AAC TCG CCC AGG CAG CTG GGA GTT ATT CTT TTT GAA AAA   1488
 F   N   L   N   S   P   R   Q   L   G   V   I   L   F   E   K    496
```

Fig. 5.4

```
CTT GGG CTG CCG GTA ATT AAA AAG ACC AAA ACG GGC TAC TCT ACC GAT   1536
 L   G   L   P   V   I   K   K   T   K   T   G   Y   S   T   D    512
GCG GAG GTT TTG GAA GAG CTC TTG CCT TTC CAC GAA ATT ATC GGC AAA   1584
 A   E   V   L   E   E   L   L   P   F   H   E   I   I   G   K    528
ATA TTG AAT TAC CGG CAG CAG CTT ATG AAG TTA AAA TCC TAC ACT GAC   1632
 I   L   N   Y   R   Q   Q   L   M   K   L   K   S   Y   T   D    544
GGC TTA ATG CCT TTA ATA AAT GAG CGT ACC GGT AAA CTG CAC ACT ACT   1680
 G   L   M   P   L   I   N   E   R   T   G   K   L   H   T   T    560
TTT AAC CAG ACC GGT ACT TTA ACC GGA CGC TTG GAA CTC TCG GAG CCC   1728
 F   N   Q   T   G   T   L   T   G   R   L   E   L   S   E   P    576
AAT CTC CAA AAT ATT CCC ATC CGG TTG GAA TAT GAT TAT GTT TCG AAA   1776
 N   L   Q   N   I   P   I   R   L   E   Y   D   Y   V   S   K    592
AAG ATG TTT ATA CCT TCA CCG GGG TAT GAT TAT ATT CGG TTA CGC       1824
 K   M   F   I   P   S   P   G   Y   D   Y   I   R   L   R        608
TAT TCC CAG ATT GAA TTA AGG CTT CTT GCC CAT TTT TCC GAA GAG CCC   1872
 Y   S   Q   I   E   L   R   L   L   A   H   F   S   E   E   P    624
```

Fig. 5.5

```
AAG CTT ATT GAA GCT TAC CAA AAA GGG GAG GAT ATT CAC CGG AAA ACG   1920
 K   L   I   E   A   Y   Q   K   G   E   D   I   H   R   K   T    640
GCC TCC GAG GTG TTC GGT GTA TCT TTG GAA GAA GTT ACT CCC GAG ATG   1968
 A   S   E   V   F   G   V   S   L   E   E   V   T   P   E   M    656
CGC GCT CAT GCC AAG TCG GTG AAC TTC GGC ATT GTT TAT GGC ATT AGT   2016
 R   A   H   A   K   S   V   N   F   G   I   V   Y   G   I   S    672
GAT TTT GGT TTA AAT TAT TTT GCC AAC TTA AAG GGA TAT CCC CGG GGT   2064
 D   F   G   L   N   Y   F   A   N   L   K   G   Y   P   R   G    688
AAG TAC ATT AAA AAT TAT TAT GCA AGA GAA AAG GGA TAT GTG GAG TAT   2112
 K   Y   I   K   N   Y   Y   A   R   E   K   G   Y   V   R   Y    704
CTC GAT GAA CTT GTC CGT AGA AGA CCT GAG CTA TCT ATT CCC ACC ACT   2160
 L   D   E   L   V   R   R   R   P   E   L   S   I   P   T   T    720
TTA TTT GGG CGA AGA CGC TAT ATT CCT GAG CTA TCT TCA AAC AAC CGC   2208
 L   F   G   R   R   R   Y   I   P   E   L   S   S   N   N   R    736
ACG GTT CAG GGT TTT GGC GAA AGG ACG GCC ATG AAT ACT CCC CTT CAG   2256
 T   V   Q   G   F   G   E   R   T   A   M   N   T   P   L   Q    752
```

Fig. 5.6

| GGC | TCG | GCT | GCC | GAT | ATT | ATT | AAG | CTT | GCA | ATG | ATT | AAT | GTA | GAA | AAA | 2304 |
|---|---|---|---|---|---|---|---|---|---|---|---|---|---|---|---|---|
| G | S | A | A | D | I | I | K | L | A | M | I | N | V | E | K | 768 |
| GAA | CTT | AAA | GCC | CGT | AAG | CTT | AAG | TCC | CGG | CTC | CTT | CTT | TCG | GTG | CAC | 2352 |
| E | L | K | A | R | K | L | K | S | R | L | L | L | S | V | H | 784 |
| GAT | GAG | TTA | GTT | TTA | GAA | GTG | CCG | GCG | GAA | GAG | CTG | GAA | GAG | GTA | AAA | 2400 |
| D | E | L | V | L | E | V | P | A | E | E | L | E | E | V | K | 800 |
| GCG | CTG | GTA | AAA | GGG | GTT | ATG | GAG | TCG | GTG | GTT | GAA | CTG | AAA | GTG | CCT | 2448 |
| A | L | V | K | G | V | M | E | S | V | V | E | L | K | V | P | 816 |
| TTA | ATC | GCT | GAA | GTT | GGT | GCA | GGC | AAA | AAC | TGG | TAT | GAA | GCG | AAG | TAA | 2496 |
| L | I | A | E | V | G | A | G | K | N | W | Y | E | A | K | * | 831 |

Fig. 5.7

THERMOSTABLE DNA POLYMERASE FROM CARBOXYDOTHERMUS HYDROGENOFORMANS

The present invention relates to a thermostable enzyme which is a DNA polymerase obtainable from *Carboxydothermus hydrogenoformans*. Furthermore, the present invention relates to the field of molecular biology and provides improved methods for the replication and amplification of deoxyribonucleic acid (DNA) and ribonucleic acid (RNA) sequences. In a preferred embodiment, the invention provides a method for synthesizing a complementary DNA copy from an RNA template with a thermoreactive DNA polymerase. In another aspect, the invention provides methods for amplifying a DNA segment from an RNA or DNA template using a thermostable DNA polymerase (RT-PCR or PCR).

Heat stable DNA polymerases (EC 2.7.7.7. DNA nucleotidyltransferase. DNA-directed) have been isolated from numerous thermophilic organisms (for example: Kaledin et al. (1980). Biokimiva 45, 644–651; Kaledin et al. (1981) Biokimiva46, 1247–1254; Kaledin et al. (1982) Biokimiya 47, 1515–1521; Ruttimann et al. (1985) Eur. J. Biochem. 149, 41–46; Neuner et al. (1990) Arch. Microbiol. 153, 205–207). For some organisms, the polymerase gene has been cloned and expressed (Lawyer et al. (1989) J. Biol. Chem. 264, 6427–6437; Engelke et al. (1990) Anal. Biochem. 191, 396–400; Lundberg et al. (1991) Gene 108, 1–6; Perler et al. (1992) Proc. Natl. Acad. Sci. USA 89, 5577).

Thermophilic DNA polymerases are increasingly becoming important tools for use in molecular biology and there is growing interest in finding new polymerases which have more suitable properties and activities for use in diagnostic detection of RNA and DNA, gene cloning and DNA sequencing. At present, the thermophilic DNA polymerases mostly used for these purposes are from Thermus species like Taq polymerase from T. aquaticus (Brock et al. (1969) J. Bacteriol. 98. 289–297)

Reverse transcription is commonly performed with viral reverse transcriptases like the enzymes isolated from Avian myeloblastosis virus or Moloney murine leukemia virus, which are active in the presence of Magnesium ions but have the disadvantages to possess RNase H-activity, which destroys the template RNA during the reverse transcription reaction and have a temperature optimum at at 42° C. or 37° C., respectively.

Alternative methods are described using the reverse transcriptase activity of DNA polymerases of thermophilic organisms which are active at higher temperatures. Reverse transcription at higher temperatures is of advantage to overcome secondary structures of the RNA template which could result in premature termination of products. Thermostable DNA polymerases with reverse transcriptase activities are commonly isolated from Thermus species. These DNA polymerases however, show reverse transcriptase activity only in the presence of Manganese ions. These reaction conditions are suboptimal, because in the presence of Manganese ions the polymerase copies the template RNA with low fidelity.

Another feature of the commonly used reverse transcriptases is that they do not contain 3'-5' exonuclease activity. Therefore, misincorporated nucleotides cannot be removed and thus the cDNA copies from the template RNA may contain a significant degree of mutations.

Therefore, it is desirable to develop a reverse transcriptase
 which acts at higher temperatures to overcome secondary structures in the template to avoid premature termination of the reaction and to assure the production of cDNA without deletions
 which is active in the presence of Magnesium ions in order to prepare cDNA from RNA templates with higher fidelity and
 which has 3'-5'-exonuclease in order to remove misincorporated nucleotides before continuation of DNA synthesis and to produce a product with a low mutation frequency.

The present invention adresses these needs and provides a heat stable DNA polymerase active at higher temperatures which has reverse transcriptase activity in the presence of magnesium ions and and which has 3'-5' exonuclease activity.

It is an object of this invention to provide a polymerase enzyme (EC 2.7.7.7.), characterised in that it has reverse transcriptase activity in the presence of magnesium ions as well as in the presence of manganese ions. In another aspect the invention comprises a DNA polymerase isolated from *Carboxydothermus hydrogenoformans* (Deutsche Sammiung von Mikroorganismen und Zellkulturen GmbH, Mascheroder Weg 1b, D-38124 Braunschweig, DSM No. 8979). In a further aspect the invention comprises a DNA polymerase having reverse transcriptase activity in the presence of magnesiums ions and in the substantial absence of manganese ions. In a further aspect the invention comprises a DNA polymerase having a molecular mass of about 100 to 105 kDa as determined by in situ PAGE analysis. In a further aspect the invention comprises a reverse transcriptase which is thermostable. In a further aspect the invention comprises a DNA polymerase having 3'-5'-exonuclease activity. In a further aspect the invention comprises a recombinant DNA sequence that encodes DNA polymerase activity of the microorganism *Carboxidothermus hydrogenoformans*. In a related aspect the DNA sequence is depicted as SEQ ID No. 7. In a second related aspect the invention comprises a recombinant DNA sequence that encodes essentially amino acid residues 1 to 831. In a further aspect the invention comprises a recombinant DNA plasmid that comprises the DNA sequence of the invention inserted into plasmid vectors and which can be used to drive the expression of the thermostable DNA polymerase of *Carboxydothermus hydrogenoformans* in a host cell transformed with the plasmid. In a further aspect the invention includes a recombinant strain comprising the vector pDS56 carrying the *Carboxydothermus hydrogenoformans* DNA polymerase gene and designated pAR 4. The *E.coli* strain (BL21 DE3)pUBS520) carrying the plasmid pAR4 was deposited on the Deutsche Sammlung von Mikroorganismen und Zellkulturen GmbH, Mascheroder Weg 1b, D-38124 Braunschweig DSM No. 11179) and is designated AR96.

In referring to a peptide chain as being comprised of a series of amino acids "substantially or effectively" in accordance with a list offering no alternatives within itself, we include within that reference any versions of the peptide chain bearing substitutions made to one or more amino acids in such a way that the overall structure and the overall function of the protein composed of that peptide chain is substantially the same as—or undetectably different to—that of the unsubstituted version. For example it is generally possible to exchange alanine and valine without greatly changing the properties of the protein, especially if the changed site or sites are at positions not critical to the morphology of the folded protein.

The DNA polymerase is "thermostable" meaning that it is stable to heat and preferentially active at higher temperatures, especially the high temperatures used for denaturation of DNA strands. More particularly, the thermostable DNA polymerases are not substantially inactivated at the high temperatures used in polymerase chain reactions.

The term "reverse transcriptase" describes a class of polymerases characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation.

Other definitions are used in a manner consistent with the art.

*Carboxydothermus hydrogenoformans* was isolated from a hot spring in Kamchatka by V. Svetlichny. A sample of *C. hydrogenoformans* was deposited on the Deutsche Sammlung von Mikroorganismen und Zelikulturen GmbH (DSM) under the terms of the BudaPest Treaty and received Accession Number DSM 8979. The thermostable polymerase isolated from *Carboxydothermus hydrogenoformans* has a molecular weight of 100 to 105 KDa and retains more than 60% of its initial activity after heating to 95° C. for 30 minutes. The thermostable enzyme possesses a 5'-3' polymerase activity, a 3'-5'-exonuclease activity, a 5'-3'-exonuclease activity and a reverse transcriptase-activity which is $Mg^{++}$-dependent. The polymerase according to the present invention has reverse transcriptase activity in the presence of magnesium ions and in the substantial absence of manganese ions. The thermostable enzyme may be native or recombinant and may be used for first- and second-strand cDNA synthesis, in cDNA cloning, DNA sequencing, DNA labeling and DNA amplification.

For recovering the native protein *C.hydrogenoformans* may be grown using any suitable technique, such as the technique described by Svetlichny et al. (1991) System. Appl. Microbiol., 14, 205–208. After cell growth one preferred method for isolation and purification of the enzyme is accomplished using the multi-step process as follows:

The cells are thawed, suspended in buffer A (40 mM Tris-HCl, pH 7.5, 0.1 mM EDTA, 7 mM 2-mercaptoethanol. 0.4 M NaCl, 10 mM Pefabloc) and lysed by twofold passage through a Gaulin homogenizer. The raw extract is cleared by centrifugation, the supernatant dialyzed against buffer B (40 mM Tris-HCl, pH 7.5, 0.1 mM EDTA, 7 mM 2-mercaptoethanol, 10% Glycerol) and brought onto a column filled with Heparin-Sepharose (Pharmacia). In each case the columns are equilibrated with the starting solvent and after the application of the sample washed with the threefold of its volume with this solvent. Elution of the first column is performed with a linear gradient of 0 to 0.5 M NaCl in Buffer B. The fractions showing polymerase activity are pooled and ammonium sulfate is added to a final concentration of 20%. This solution is applied to a hydrophobic column containing Butyl-TSK-Toyopearl (TosoHaas). This time the column is eluted with a falling gradient of 20 to 0% ammonium sulfate. The pool containing the activity is dialysed and again transferred to a column, this time with DEAE-Sepharose (Pharmacia), and eluted with a linear gradient of 0–0.5 M NaCl in buffer B. The fourth column contains Tris-Acryl-Blue. (Biosepra) and is eluted as in the preceding case.

Finally the active fractions are dialyzed against buffer C (20 mM Tris-HCl, pH 7.5, 0.1 mM EDTA, 7.0 mM 2-mercaptoethanol. 100 mM NaCl, 50% Glycerol.

Isolation of recombinant DNA polymerase from *Carboxydothermus hydrogenoformans* may be performed with the same protocol or with other commonly used procedures.

DNA polymerase activity was measured by incorporation of digoxigenin-labeled dUTP into the sythesized DNA and detection and quantification of the incorporated digoxigenin essentially according to the method described in Hölke, H.-J.; Sagner, G; Kessler, C. and Schmitz. G. (1992) Biotechniques 12, 104–113.

Determination of reverse transcriptase activity is performed essentially as described for determination of DNA polymerase activity except that the reaction mixture consists of the components as described by example 3. In situ PAGE analysis of polymerase activity and reverse transcriptase activity was performed essentially according to the method described by Spanos A. and Hübscher U. ((1983) Methods in Enzymology 91, 263–277). Some minor, but essential modifications to the original method are, that the renaturation of the SDS-denatured polypeptides is performed in the presence of magnesium ions (3 mM) and dATP (0.5–1 $\mu$M) to assist refolding.

3'-5' exonuclease activity is commonly referred as "proof-reading" or "editing" activity of DNA polymerases. It is located in the small domain of the large fragment of Type A polymerases. This activity removes mispaired nucleotides from the 3' end of the primer terminus of DNA in the absence of nucleoside triphosphates (Kornberg A. and Baker T. A.(1992) DNA Replication W. H. Freemann & Company, New York). This nuclease action is suppressed by deoxynucleoside triphosphates if they match to the template and can be incorporated into the polymer.

The 3'- 5' exonuclease activity of the claimed DNA polymerase can be measured as degradation or shortening of a 5'-digoxygenin-labeled oligonucleotide annealed to template DNA in the absence or presence of deoxyribonucleoside triphosphates or on DNA fragments in the absence or presence of deoxyribonucleoside triphosphates.

*Carboxydothermus hydrogenoformans* DNA polymerase is the first DNA polymerase isolated from thermophilic eubacteria with a higher activity in the presence of magnesium ions than in the presence of manganese ions as shown in FIG. 1. Compared to the DNA polymerase activity the reverse transcriptase activity in the presence of magnesium is relatively high. This is shown—in comparison with DNA polymerases from *T.filiformis*, *A.thermophilum* and the most commonly used DNA polymerase for reverse transcription *T.thermophilus* in FIG. 6. The reverse transcriptase activity in dependence of magnesium is of advantage since the DNA polymerases synthesize DNA with higher fidelity in the presence of magnesium than in the presence of manganese (Beckmann R. A. et al. (1985) Biochemistry 24, 5810–5817; Ricchetti M. and Buc H. (1993) EMBO J. 12, 387–396). Low fidelity DNA synthesis is likely to lead to mutated copies of the original template. In addition, $Mn^{2+}$ ions have been implicated in an increased rate of RNA degradation, particularly at higher temperatures and this can cause the synthesis of shortened products in the reverse transcription reaction.

The DNA sequence (SEQ ID No.: 7) of *Carboxydothermus hydrogenoformans* polymerase and the derived amino acid sequence of the enzyme are shown in FIG. 5. The molecular weight deduced from the sequence is 94 348 Da, in SDS polyacrylamide gel electrophoresis however the *Carboxydothermus hydrogenoformans* polymerase has an electrophoretic mobility higher than *E.coli* pol I (109 kDa) and a lower mobility than Taq polymerase (94 kDa) and Klenow fragment (76 kDa) as shown in FIG. 2. Comparing the migration properties of Taq and *E.coli* DNA polymerases with those of *Carboxydothermus hydrogenoformans* polymerase a molecular weight of 100 to 105 kDa can be deduced. Since the *Carboxydothermus hydrogenoformans* polymerase isolated from the native strain has the same migration properties as the recombinant enzyme the "slower" migration during SDS gel electrophoresis must rather be a property of the enzyme than a cloning artefact. A possible explanation for this phenomenon could be that this enzyme which is derived from a thermophilic organism has a very stable structure which is not completely unfolded under the standard denaturation conditions used.

The production of a recombinant form of *Carboxydothermus hydrogenoformans* DNA polymerase generally includes the following steps: chromosomal DNA from *Carboxydothermus hydrogenoformans* is isolated by treating the cells with detergent e.g. SDS and a proteinase e.g. Proteinase K. The solution is extracted with phenol and chloroform and the DNA purified by precipitation with ethanol. The DNA is dissolved in Tris/EDTA buffer and the gene encoding the DNA polymerase is specifically amplified by the PCR technique using two mixed oligonucleotides (primer 1 and 2). These oligo-nucleotides. described by SEQ ID No.: 1 and SEQ ID No.: 2. were designed on the basis of conserved regions of family A DNA polymerases as published by Braithwaite D. K. and Ito J., 1993, Nucl. Acids Res. Vol. 21, p. 787–802. The specifically amplified fragment is ligated into an vector, preferably the pCR™ II vector (Invitrogen) and the sequence is determined by cycle-sequencing. Complete isolation of the coding region and the flanking sequences of the DNA polymerase gene can be performed by restriction fragmentation of the *Carboxydothermus hydrogenoformans* DNA with another restriction enzyme as in the first round of screening and by inverse PCR (Innis et al., (1990) PCR Protocols; Academic Press, Inc., p. 219–227). This can be accomplished with synthesized oligonucleotide primers binding at the outer DNA sequences of the gene part but in opposite orientation. These oligonucleotides described by SEQ ID Nos. 3 and 4, were designed on the basis of the sequences which were determined by sequencing of the first PCR product described above. As template *Carboxydothermus hydrogenoformans* DNA is used which is cleaved by restriction digestion and circularized by contacting with T4 DNA ligase. To isolate the coding region of the whole polymerase gene, another PCR is performed using primers as shown in SEQ ID Nos. 5 and 6 to amplify the complete DNA polymerase gene directly from genomic DNA and introducing ends compatible with the linearized expression vector.

SEQ ID No. 1:
   Primer 1: 5'-CCN AAY YTN CAR AAY ATH-3'
SEQ ID No. 2:
   Primer 2: 5'-YTC RTC RTG NAC YTG-3'
SEQ ID No. 3:
   Primer 3: 5'-GGG CGA AGA CGC TAT ATT CCT GAG C-3'
SEQ ID NO. 4:
   Primer 4: 5'-GAA GCC TTA ATT CAA TCT GGG AAT AAT C-3'
SEQ ID NO. 5:
   Primer 5: 5'-CGA ATT CAA TCC ATG GGA AAA GTA GTC CTG GTG GAT-3'
SEQ ID NO. 6:
   Primer 6: 5'-CGA ATT CAA GGA TCC TTA CTT CGC TTC ATA CCA GTT-3'

The gene is operably linked to appropriate control sequences for expression in either prokaryotic or eucaryotic host/vector systems. The vector preferably encodes all functions required for transformation and maintenance in a suitable host, and may encode selectable markers and/or control sequences for polymerase expression. Active recombinant thermostable polymerase can be produced by transformed host cultures either continuously or after, induction of expression. Active thermostable polymerase can be recovered either from host cells or from the culture media if the protein is secreted through the cell membrane.

It is also preferable that *Carboxydothermus hydrogenoformans* thermostable polymerase expression is tightly controlled in *E.coli* during cloning and expression. Vectors useful in practicing the present invention should provide varying degrees of controlled expression of *Carboxydothermus hydrogenoformans* polymerase by providing some or all of the following control features: (1) promoters or sites of initiation of transcription, either directly adjacent to the start of the polymerase gene or as fusion proteins, (2) operators which could be used to turn gene expression on or off, (3) ribosome binding sites for improved translation, and (4) transcription or translation termination sites for improved stability. Appropriate vectors used in cloning and expression of *Carboxydothermus hydrogenoformans* polymerase include, for example, phage and plasmids. Example of phage include lambda gtII (Promega), lambda Dash (Stratagene) lambda ZapII (Strata-gene). Examples of plasmids include pBR322, pBTac2 (Boehringer Mannheim), pBluescript (Stratagene), pSP73 (Promega), pET3A (Rosenberg, supra, (1987) Gene 56:125–135), pASK75 (Biometra), pDS56 (Stüber, D., Matile, H. and Garotta G. (1990) Immunological Methods, Letkovcs, I. and Pernis, B., eds.) and pET11C (Studier, F. W. (1990) Methods in Enzymology, 185:60–89). According to the present invention the use of a plasmid has shown to be advantageously, particularly pDS56. The Plasmid pDS56 carrying the *Carboxydothermus hydrogenoformans* DNA polymerase gene is then designated pAR4.

Standard protocols exist for transformation, phage infection and cell culture (Maniatis, et al. (1982) Molecular Cloning: A Laboratory Manual, Cold Spring Harbour Laboratory Press). Of the numerous *E.coli* strains which can be used for plasmid transformation, the preferred strains include JM110 (ATCC 47013), LE392 pUBS 520 (Maniatis et al. supra; Brinkmann et al., (1989) Gene 85:109–114;), JM101 (ATCC No. 33876), XL1 (Stratagene), and RR1 (ATCC no. 31343), BL21 (DE3) pUBS520 (Brinkmann, U. et al. (1989) Gene 85, 109–114) and BL21 (DE3) plysS (Studier, F. W. et al., (1990) Methods in Enzymology, supra). According to the present invention the use of the *E. coli* strain BL21 (DE3) pUBS520 has shown to be advantageously. The *E. coli* strain BL21 (DE3) pUBS520 transformed with the plasmid pAR4 is then designated AR96 (DSM No. 11179). *E.coli* strains XL1-Blue (Stratagene), and ER1458 (Raleigh, E. A. et al., (1988) Nucleic Acids Research 16:1563–1575) are among the strains that can be used for lambda phage, and Y1089 can be used for lambda gt11 lysogeny. The transformed cells are preferably grown at 37° C. and expression of the cloned gene is induced with IPTG.

Isolation of the recombinant DNA polymerase can be performed by standard techniques. Separation and purification of the DNA polymerase from the *E.coli* extract can be performed by standard methods. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electric charge such as ion-exchange column chromatography, methods utilizing specific interaction such as affinity chromatography, methods utilizing a difference in hydrophobicity such as reversed-phase high performance liquid chromatography and methods utilizing a difference in isoelectric point such as isoelectric focussing electrophoresis.

The present invention provides improved methods for efficiently transcribing RNA and amplifying RNA or DNA. These improvements are achieved by the discovery and application of previously unknown properties of thermoactive DNA polymerases.

The thermostable enzyme of this invention may be used for any purpose in which such enzyme activity is necessary or desired. In a particularly preferred embodiment, the enzyme catalyzes the nucleic acid amplification reaction known as PCR. This process for amplifying nucleic acid sequences is disclosed and claimed in U.S. Pat. No. 4,683, 202. The PCR nucleic acid amplification method involves amplifying at least one specific nucleic acid sequence contained in a nucleic acid or a mixture of nucleic acids and produces double-stranded DNA. Any nucleic acid sequence, in purified or nonpurified form, can be utilized as the starting nucleic acid(s), provided it contains or is suspected to contain the specific nucleic acid sequence desired. The nucleic acid to be amplified can be obtained from any source, for example, from plasmids such as pBR322, from cloned DNA or RNA, from natural DNA or RNA from any source, including bacteria, yeast, viruses, organelles, and higher organisms such as plants and animals, or from preparations of nucleic acids made in vitro.

DNA or RNA may be extracted from blood, tissue material such as *chorionic villi*, or amniotic cells by a variety of techniques. See, e.g., Maniatis et al., 1982, Molecular Cloning: A Laboratory Manual (Cold Spring Harbor Laboratory, Cold Spring Harbor, N.Y.) pp. 280–281. Thus the process may employ, for example, DNA or RNA, including messenger RNA, which DNA or RNA may be single-stranded or double-stranded. In addition, a DNA-RNA hybrid which contains one strand of each may be utilized.

The amplification of target sequences in DNA or from RNA may be performed to proof the presence of a particular sequence in the sample of nucleic acid to be analyzed or to clone a specific gene. DNA polymerase from *Carboxydothermus hydrogenoformans* is very useful for these processes. Due to its 3'-5' exonuclease activity it is able to synthesize products with higher accuracy as the reverse transcriptases of the state of the art.

DNA polymerase from *Carboxydothermus hydrogenoformans* may also be used to simplify and improve methods for detection of RNA target molecules in a sample. In these methods DNA polymerase from *Carboxydothermus hydrogenoformans* may catalyze: (a) reverse transcription, (b) second strand cDNA synthesis, and. if desired, (c) amplification by PCR The use of DNA polymerase from *Carboxydothermus hydrogenoformans* in the described methods would eliminate the previous requirement of two sets of incubation conditions which are necessary due to the use of different enzymes for each step. The use of DNA polymerase from *Carboxydothermus hydrogenoformans* may be used to perform RNA reverse transcription and amplification of the resulting complementary DNA with enhanced specificity and with fewer steps than previous RNA cloning and diagnostic methods.

BRIEF DESCRIPTION OF THE DRAWINGS

FIG. 5 shows the DNA sequence of the polymerase gene of *Carboxydothermus hydrogenoformans* with SEQ ID No.: 7 and the derived peptide sequence of the DNA polymerase protein with SEQ ID No. 8.

EXAMPLE 1

Figure 1:
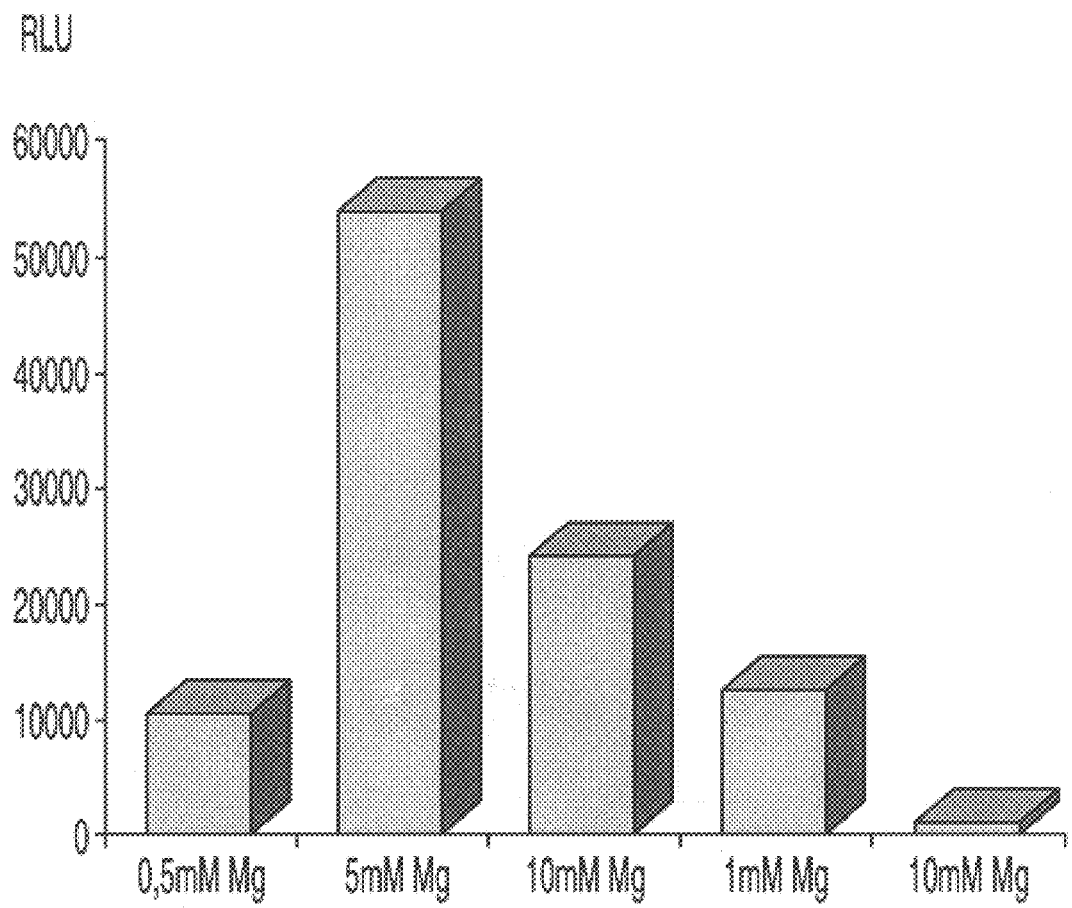
FIG. 1 shows the relative reverse transcriptase activity of DNA polymerase from *Carboxydothermus hydrogenoformans* in dependence of magnesium and manganese salt.
Figure 2:
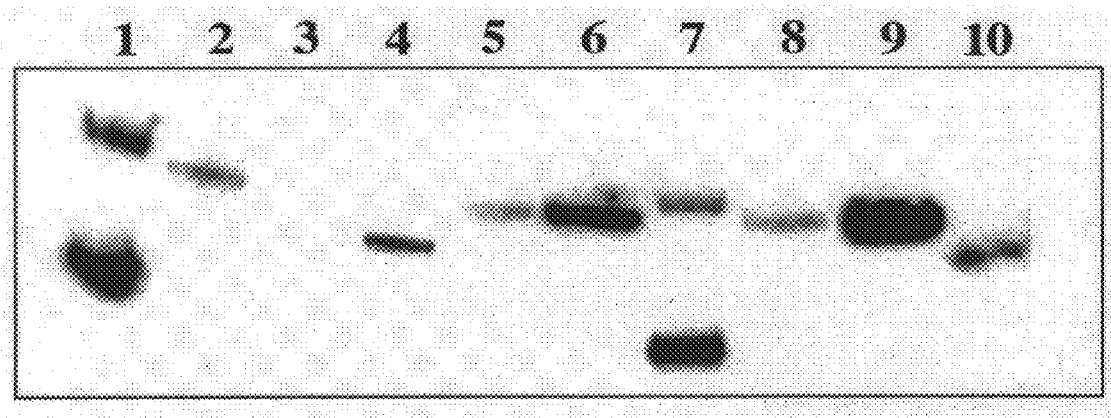
FIG. 2 shows a photograph of a DNA polymerase assay performed in situ. The activity of DNA polymerase from *Carboxydothermus hydrogenoformans* and reference polymerases is detected in situ. A fraction of DNA polymerase from *C. hydrogenoformans* and reference enzyme were submitted to electrophoresis on a SDS-polyacrylamide gel containing activated calf thymus DNA. After electrophoresis the SDS was removed, the proteins were renatured and incubated at 65° C. in the presence of magnesium salt, dNTPs and digoxigenin labeled dUTP to allow DNA synthesis. The nucleic acid was blotted to a nylon membrane and the newly synthesized DNA detected by a chemiluminescence reaction.
Figure 3:
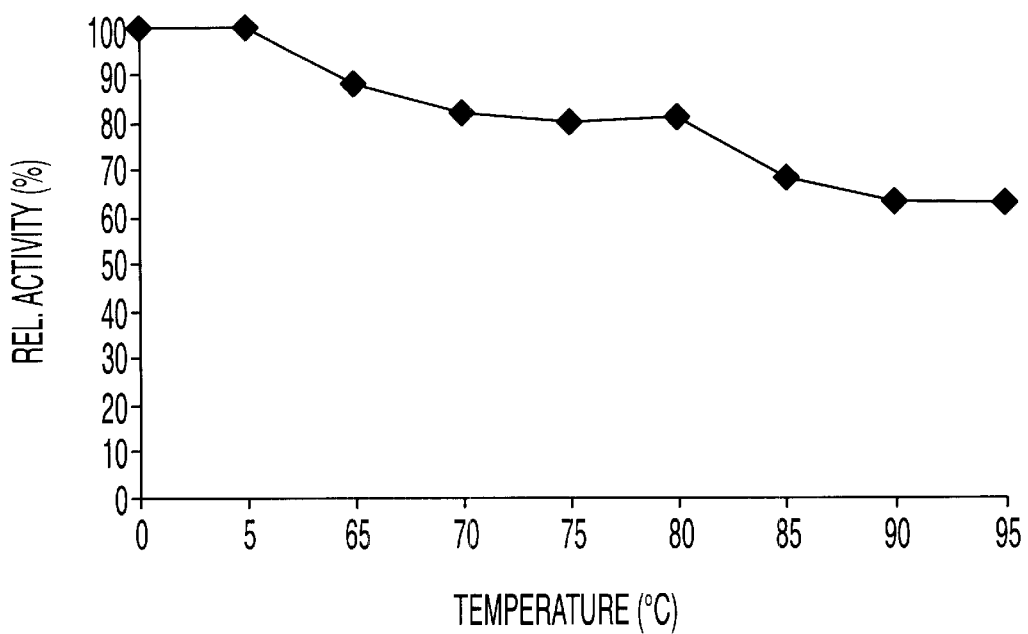
FIG. 3 shows the thermostability of DNA polymerase from *Carboxydothermus hydrogenoformans*. Aliquots of the DNA polymerase were incubated for 30 min. at the temperatures indicated in the figure, and subsequently the remaining enzyme activity was determined.
Figure 4:
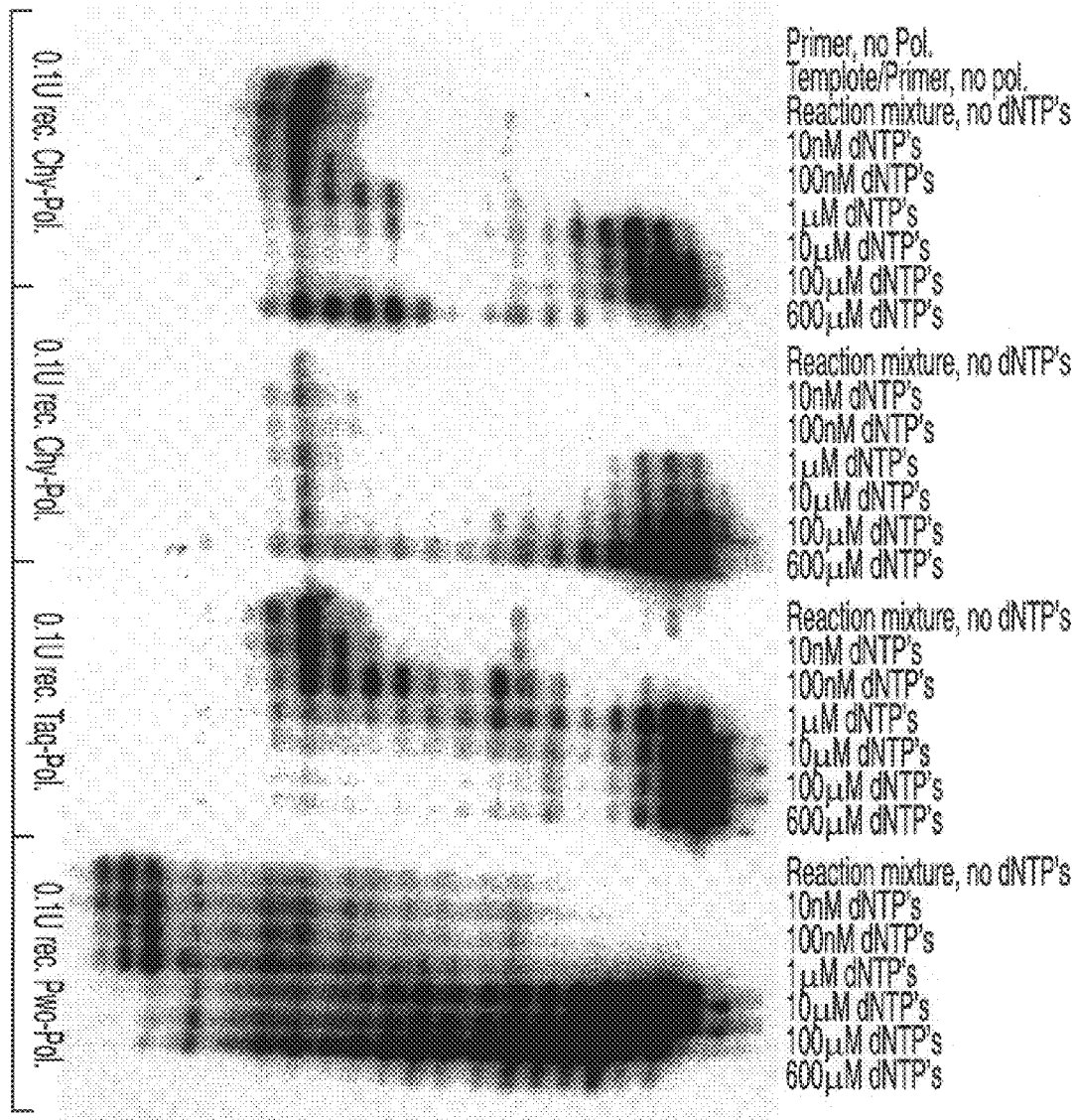
FIG. 4 shows the analysis for 3'-5'-exonuclease activity of DNA polymerase from *Carboxydothermus hydrogenoformans* in comparison with DNA polymerase from *Thermus aquaticus* and *Pyrococcus woeseii*. The analysis is performed in the presence or absence of dNTPs. A 22mer primer labeled with digoxigenin at the 5'-end was annealed to a 34mer template DNA leaving a 12 bp 5' overhang of template DNA. DNA polymerases from *Carboxydothermus hydrogenoformans*, *Thermus aquaticus* and *Pyrococcus woeseii* were incubated with this substrate in the presence of magnesium with or without dNTPs. The products were separated on a sequencing gel, blotted to a nylon membrane and detected by a chemiluminescence reaction.
Figure 6:
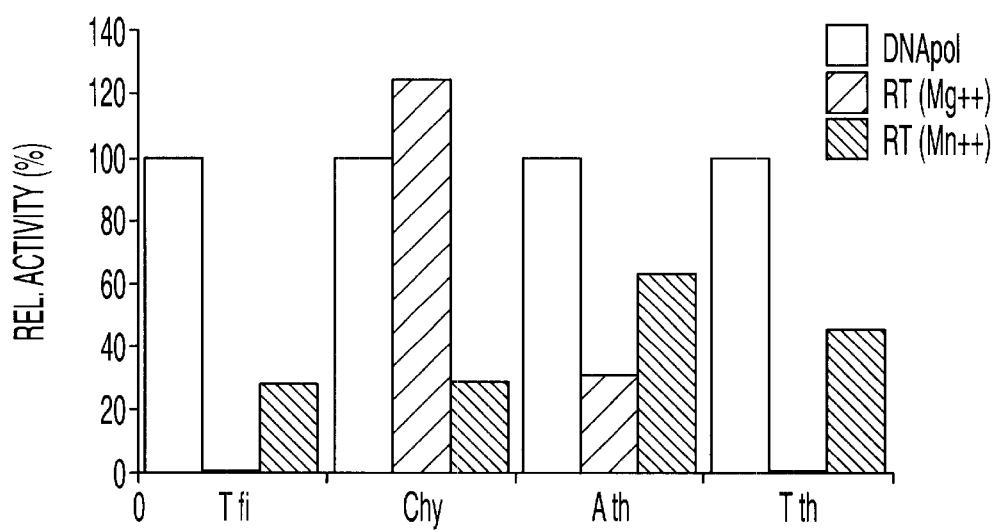
FIG. 6 shows a comparison of the reverse transcriptase activity thermostable DNA polymerases *Carboxydothermus hydrogenoformans*, *Anaerocellum thermophilum*, *Thermus filiformis* (Pacific Enzymes) and *Thermus thermophilus*. Similar amounts (units) of the DNA polymerases were analyzed. Each enzyme was tested for DNA polymerase activity, for reverse tanscriptase activity in the presence of $Mg^{++}$ (5 mM) and reverse transcriptase activity in the presence of $Mn^{++}$ (1 mM) under the reaction conditions optimal for the individual enzymes. DNA synthesis was measured by incorporation of digoxigenin-labeled nucleotides. In order to compare the ratio of DNA polymerase to reverse transcriptase activity, the relative light units (RLU) measured in the DNA polymerase assay was set to 100. The RLUs measured in the reverse transcriptase activity tests are expressed as percent of the polymerase activity.

Detection of Endonuclease, Exonuclease and Ribonuclease Activities

Absence of endonuclease activity: 1 µg of plasmid DNA is incubated for 4 hours with an excess of purified DNA polymerase in 50 µl of test buffer with a paraffin oil overlay at 72° C.

Absence of nonspecific exonuclease activity: 1 µg of EcoRI/HindIII-fragments of lambda DNA are incubated in 100 µl of test buffer in the absence and presence of dNTPs (1 mM final concentration each) with an excess of purified DNA polymerase for 4 hours at 72° C.

Absence of ribonuclease activity: 3 µg of MS2 RNA are incubated with an excess of DNA polymerase in 20 µl of test buffer for 4 hours at 72° C. The RNA is subsequently analyzed by electrophoresis in a MOPS gel (Maniatis et al. (1982) Molecular Cloning: A Laboratory Manual, Cold Spring Harbor, N.Y.).

EXAMPLE 2

Determination of DNA Polymerase Activity

DNA polymerase activity was measured by incorporation of digoxigenin-labeled dUTP into the sythesized DNA and detection and quantification of the incorporated digoxigenin essentially according to the method described in Höltke, H.-J.; Sagner. G. Kessler, C. and Schmitz, G. (1992) Biotechniques 12, 104–113. The reaction is performed in a reaction volume of 50 µl containing 1 or 2 µl of diluted (0.05 U–0.01 U) DNA polymerase and 50 mM Tris-HCl, pH 8.5; 12.5 mM $(NH_4)_2SO_4$; 10 mM KCl; 5 mM $MgCl_2$; 10 mM 2-mercaptoethanol; 33 µM dNTPs; 200 µg/ml BSA;12 µg of DNAse 1-activated DNA from calf thymus and 0.036 µM digoxigenin-dUTP.

The samples are incubated for 30 min. at 72° C., the reaction is stopped by addition of 2 µl 0.5 M EDTA. and the tubes placed on ice. After addition of 8 µl 5 M NaCl and 150 µl of Ethanol (precooled to –20° C.) the DNA is precipitated by incubation for 15 min. on ice and pelleted by centrifugation for 10 min at 13000×rpm and 4° C. The pellet is washed with 100 µl of 70% Ethanol (precooled to –20° C.) and 0.2 M NaCl, centrifuged again and dried under vacuum.

The pellets are dissolved in 50 µl Tris-EDTA (10 mM/0.1 mM; pH 7.5). 5 µl of the sample are spotted into a well of a nylon membrane bottomed white microwell plate (Pall Filtrationstechnik GmbH, Dreieich, FRG, product no: SM045BWP). The DNA is fixed to the membrane by baking for 10 min. at 70° C. The DNA loaded wells are filled with 100 l of 0.45 µm-filtrated 1% blocking solution (100 mM maleic acid, 150 mM NaCl, 1% (w/v) casein, pH 7.5). All following incubation steps are done at room temperature. After incubation for 2 min. the solution is sucked through the membrane with a suitable vacuum manifold at –0.4 bar. After repeating the washing step, the wells are filled with 100 µl of a 1:10 000-dilution of Anti-digoxigenin-AP, Fab fragments (Boehringer Mannheim, FRG, no: 1093274) diluted in the above blocking solution. After incubation for 2 min. and sucking this step is repeated once. The wells are washed twice under vacuum with 200 µl each time washing-buffer 1 (100 mM maleic-acid, 150 mM NaCl, 0.3%(v/v) Tween™ 20 (Poly(oxyethylen)$_n$-Sorbitan-monolaurat), pH 7.5). After washing another two times under vacuum with 200 µl each time washing-buffer 2 (10 mM Tris-HCl. 100 mM NaCl, 50 mM $MgCl_2$, pH 9.5) the wells are incubated for 5 min. with 50 µl of CSPD™ (Boehringer Mannheim. no: 1655884), diluted 1:100 in washing-buffer 2, which serves as a chemiluminescent substrate for the alkaline phosphatase. The solution is sucked through the membrane and after 10 min. incubation the RLU/s (Relative Light Unit per second) are detected in a Luminometer e.g. MicroLumat LB 96 P (EG&G Berthold, Wilbad, FRG).

With a serial dilution of Taq DNA polymerase a reference curve is prepared from which the linear range serves as a standard for the activity determination of the DNA polymerase to be analyzed.

EXAMPLE 3

Determination of Reverse Transcriptase Activity

The assay is performed essentially as described for determination of DNA polymerase activity except that the reaction mixture consists of the following components: 1 µg of polydA-$(dT)_{15}$, 33 µM of dTTP, 0.36 µM of digoxigenin-dUTP, 200 mg/ml BSA, 10 mM Tris-HCl, pH 8.5, 20 mM KCl, 5 mM $MgCl_2$, 10 mM DTE and various amounts of DNA polymerase The incubation temperature used is 50° C.

EXAMPLE 4

Detection of DNA Polymerase Activity in Situ

In situ PAGE analysis of polymerase activity and reverse transcriptase activity was performed essentially according to the method described by Spanos A. and Hübscher U. (1983) Methods in Enzymology 91, 263–277. Some minor, but essential modifications to the original method are, that the renaturation of the SDS-denatured polypeptides is performed in the presence of magnesium ions (3 mM) and DATP (0.5–1 µM) to assist refolding.

In Brief the Method is as Follows

After separation of the polypeptides from either crude cell extracts or purified samples on denaturing 8% polyacrylamide gels (stacking gel 5% acrylamide) which contain 150 µg activated calf thymus DNA per ml gel volume, the gels are washed four times for 30 min each at room temperature with moderate shaking in excess renaturation buffer (Tris-HCl, 50 mM, pH 8.3; EDTA, 1 mM; 2-mercaptoethanol, 3 mM; KCl, 50 mM; glycerol, 5–10%) to remove SDS. Then the gels are incubated overnight in the same buffer, including 3 mM $MgCl_2$ and 0.5–1 µM dATP at 4° C. without agitation. The first four washes are repeated the next day with renaturation buffer. Subsequent to the removal of SDS and renaturation of the proteins the gel is transferred into reaction mixture, consisting of Tris-HCl, 50 mM, pH 8.3; KCl, 50 mM; DTT, 3 mM; $MgCl_2$, 7 mM, 12 µM of each dATP, dCTP, dGTP, 8 µM dTTP and 4 µM Dig-dUTP; 10% (vol/vol) glycerol. Gels were first incubated under shaking at room temperature for one hour and then warmed up stepwise to 37° C., 45° C., 55° C., 65° C. and 72° C. At each incubation temperature DNA synthesis was allowed to proceed for 60 minutes.

After DNA synthesis, the DNA is transferred either by contact blotting or by capillary blotting (15×SSC, Maniatis et al., supra) to nylon membranes (Boehringer Mannheim, GmbH) and crosslinked.

The detection of newly synthesized, digoxigenin-labeled DNA followed the procedure given in the previous section (Determination of DNA polymerase activity).

For molecular weight determination marker polymerases of known molecular weight (e.g. Klenow-polymerase, Pol I, Taq polymerase, Tth polymerase, HIV RT, M-MuLV RT) are applied onto the same gel, but different lanes.

The molecular weight of the claimed DNA polymerase according to this method is 100 to 105 kDa.

EXAMPLE 5

Detection of 3'-5' Exonuclease Activity

3'-5 exonuclease activity is commonly referred as "proof-reading" or "editing" activity of DNA polymerases. It is located in the small domain of the large fragment of Type A polymerases. This activity removes nucleotides from the 3' end of the primer terminus of DNA in the absence of nucleoside triphosphates (Komberg A. and Baker T. A.(1992) DNA Replication W. H. Freemann & Company, New York). This nuclease action is suppressed by deoxynucleoside triphosphates if they match to the template and can be incorporated into the polymer.

The 3'-5' exonuclease activity of the claimed DNA polymerase can be measured as degradation or shortening of a 5'-digoxygenin-labeled oligonucleotide annealed to template DNA in the absence or presence of deoxyribonucleoside triphosphates or on DNA fragments in the absence or presence of deoxyribonucleoside triphosphates.

Degradation of digoxigenin labeled oligonucleotide: The reaction mixture is essentially the same as that for determination of DNA polymerase activity (50 mM Tris-HCl, pH 8.4, 12.5 mM $(NH_4)_2SO_4$; 10 mM KCl; 5 mM $MgCl_2$ 10 mM 2-mercaptoethanol), except that the dNTP concentration was reduced to 12.5 μM and activated calf thymus DNA was replaced by 500 fMol primer or template/primer mixture.

The primer sequence is:
SEQ ID NO.8.:
Dig-GCATGGATCCCACTGCCCAGGG (5' to 3').

This primer is annealed with template molecules of various 12 bp 5 prime overhangs. DNA polymerase samples of typically 0.1 units are incubated in a total reaction volume of 10 μl for 30 min at 72° C. in a Perkin Elmer thermal cycler. Reactions are stopped by adding an equal volume of formamide-buffer (98% formamide; 10 mM EDTA; bromphenol blue and xylencyanol) and denatured by heating for 10 min at 95° C. Samples are quickly chilled on ice and loaded on a 20% denaturing polyacrylamide/urea sequencing gel. Electrophoresis is performed at 60° C. and 2000 V for 2.5 hours.

After separation DNA is transferred onto a positively charged nylon membrane (Boehringer Mannheim) by contact blotting for 30 min. The DNA is crosslinked to the membrane by UV-irradiation with 120 mJoule (Stratalinker. Stratagene). The membrane is blocked with blocking solution (100 mM maleic-acid, 150 mM NaCl, 1%(w/v) casein. pH is adjusted to 7.5 with 1 M NaOH) at room temperature for at least 30 min. digoxigenin-labeled primer DNA is detected with anti Digoxigenin-AP. Fab-fragments (Boehringer Mannheim, FRG, no 1093274) diluted 1:10000 in blocking solution (30 min at room temperature). Excess unbound antibody is removed by washing 3–4 times (10–15 min, each step) with washing buffer (100 mM maleic-acid, 150 mM NaCl, 0.3% (v/v) Tween™ 20 (Poly(oxyethylen)$_n$-sorbitan-monolaurat), pH 7.5). The membrane is transferred into a buffer containing 10 mM Tris-HCl, 100 mM NaCl, pH 9.5) and washed twice for additional 10–15 min at room temperature. Finally the membrane is soaked with a 1:1000 diluted solution of CDP-Star™ (Boehringer Mannheim). CDP-Star™ serves as a chemiluminiscent substrate for alkaline phosphatase. Then the membrane is transferred on filter paper (Whatman 3MM) to remove excess fluid, positioned between two sheets of transparent overhead foils and exposed to X-ray film. (Chemiluminescent Detection Film, Boehringer Mannheim) for 5–10 min. 3'-5' exonuclease activity is detected by degradation or shortening of the primer compared with a control (no polymerase added). As negative and positive controls DNA polymerases from *Thermus aquaticus* (no 3' to 5' exonuclease activity) and from *Pyrococcus woeseii* (exhibiting 3' to 5' exonuclease activity) are included.

Degradation of DNA fragments in the presence or absence of deoxynucleoside triphosphates: A series of dilutions of Chy polymerase was incubated for 2 hours at 70° C. with 1 μg of DNA molecular weight marker III (Boehringer Mannheim) in the presence and absence of dNTPs, 1 mM each, in 50 μl of the following incubation buffer: 50 mM Tris-HCl, pH 7.8; 10 mM $MgCl_2$; 7 mM 2-mercaptoethanol with Paraffin overlay. The DNA fragments were separated on a 1% agarose gel containing ethidium bromide. In the absence of dNTPs a smear of DNA fragments or no DNA could be detected while in the presence of dNTPs the DNA fragments remained undegraded.

EXAMPLE 6

Cloning of the *Carboxydothermus hydrogenoformans* DNA Polymerase Gene

Preparation of chromosomal DNA from *Carboxydothermus hydrogenoformans*. 0.8 g biomass of Carboxydothermus hydrogenoformans was suspended in 20 ml 1 M KCl and centrifuged. Then the pellet was resuspended in 4.8 ml SET-buffer (150 mM NaCl, 15 mM EDTA, pH 8.0, 60 mM Tris-HCl, pH 8.0, 50 μg/μl RNaseA), after which 1 ml 20% SDS and 50 μg of proteinase K (10 mg/ml) were added. The mixture was kept at 37° C. for 45 minutes. After extraction with phenol and chloroform the DNA was precipitated with ethanol and dissolved in $H_2O$. Thus about 4.1 mg of DNA were obtained.

Amplification of Specific DNA by PCR

For amplification of the gene encoding the DNA polymerase of *Carboxydothermus hydrogenoformans* by the PCR technique two mixed oligonucleotides (primer 1 and 2) were designed on the basis of conserved regions of family A DNA polymerases as published by Braithwaite D. K. and Ito J. (1993) Nucl. Acids Res. 21, 787–802.

SEQ ID No.: 1
Primer 1: 5'-CCN AAY YTN CAR AAY ATH-3'
SEQ ID No.: 2
Primer 2: 5'-YTC RTC RTG NAC YTG-3'

The PCR amplification was performed in 100 μl buffer containing 750 ng of genomic DNA from *Carboxydothermus hydrogenoformans,* 10 mM Tris-HCl, pH 8.8. 2.5 mM $MgCl_2$, 50 mM KCl, 200 μM dNTPs, 100 pmoles of each primer and 2.5 units of Taq polymerase (Boehringer Mannheim GmbH, FRG). The target sequence was amplified by first denaturing at 95° C. for 2 min. followed by 30 cycles of 95° C. for 0.5 min. 47° C. for 1 min. and 72° C. for 2 minutes. Thermal cycling was performed in a Perkin Elmer GenAmp 9600 thermal cycler. Agarose gel electrophoresis showed, that a fragment of approximately 600 base pairs was amplified specifically. This fragment was ligated into the pCR™ II vector (Invitrogen) and the sequence determined by cycle-sequencing. The amino acid sequence deduced from this nucleotide sequence was very similar to that of other known DNA polymerases, so that primer 3 and 4 could be designed for inverse PCR.

SEQ ID No.: 3
Primer 3: 5'-GGG CGA AGA CGC TAT ATT CCT GAG C-3'
SEQ ID No.: 4
Primer 4: 5'-GAA GCC TTA ATT CAA TCT GGG AAT AAT C-3'

Inverse PCR was performed essentially as described in Triglia T. et al. (1988) Nucleic Acids Res. 16, 8186. 5 μg genomic DNA from *Carboxydothermus hydrogenoformans* were cleaved by EcoRI according to supplier's specifications (Boehringer Mannheim GmbH) and treated with an equal volume of phenol/chloroform mixture. The aqueous phase was removed, the DNA precipitated with ethanol and collected by centrifugation.

For circularization the digested DNA was diluted to a concentration of 50 ng/μl in ligation buffer (Boehringer Mannheim GmbH, FRG). The ligation reaction was initiated by the addition of T4 DNA Ligase (Boehringer Mannheim GmbH, FRG) to a concentration of 0.2 units/μl and the reaction was allowed to proceed for 15 hrs at 15° C. The ligated DNA was then precipitated with ethanol and collected by centrifugation.

The PCR was performed in 50 μl buffer containing 50 mM Tris-Cl, pH 9.2, 16 mM $(NH_4)_2SO_4$, 2.25 mM $MgCl_2$, 2% (v/v) DMSO, 0.1% (v/v) Tween™ 20, 700 ng of circularized DNA obtained as described above, 50 pmoles of each primer. 500 μM dNTP and 0.75 μl enzyme mix (Expand Long Template PCR System, Boehringer Mannheim GmbH).

The cycle conditions were as follows:

1×denaturation of template for 2 min. at 92° C.

10× {denaturation at 92° C. for 10 sec.; annealing at 64° C. for 30 sec.; elongation at 68° C. for 2 min.}

20× {denaturation at 92° C. for 10 sec.; annealing at 64° C. for 30 sec.; elongation at 68° C. for 2 min.+ cycle elongation of 20 sec. for each cycle}

Agarose gel electrophoresis revealed a specifically amplified DNA fragment 7.000 base pairs long. The DNA fragment was ligated into the pCR™ II vector (Invitrogen) and sequenced. Deduced from this sequence primer 5 and 6 coding for the 5'- and 3'-ends, respectively, of the polymerase region could be designed. Primer 5 contained a NcoI site and primer 6 contained a BamHI site. The PCR was performed under the same conditions as described above (inverse PCR) using 750 ng genomic DNA from *Carboxydothermus hydrogenoformans* as template.

SEQ ID No.: 5

Primer 5: 5'-CGA ATT CAA TCC ATG GGA AAA GTA GTC CTG GTG GAT-3'

SEQ ID No.: 6

Primer 6: 5'-CGA ATT CAA GGA TCC TTA CTT CGC TTC ATA CCA GTT-3'

Cloning and Expression

The PCR product was purified by electrophoresis of 20 μl of the PCR mixture on a 0.8% agarose gel. The 2.496 kb band of the polymerase coding region was purified from the agarose by phenol extraction. The DNA was then treated with chloroform and precipitated with ethanol. The pellet was resuspended and digested with NcoI and BamHI according to supplier's specifications (Boehringer Mannheim GmbH) to give cohesive ends for directional cloning. The DNA was ligated into the expression vector pDS56 (Stüber D., Matile H. and Garotta G. (1990) Immunological Methods, Letkovcs, I and Penis, B., eds.) that had also been digested with NcoI and BamHI. The ligated products were introduced into *E.coli* strain BL21(DE3) pUBS520 (Brinkmann U. et at. (1989) Gene 85, 109–114) by transformation. Transformants were grown on L-agar containing 100 μg/ml ampicillin and 50 μg/ml kanamycin to allow selection of recombinants. Colonies were picked and grown in L-broth containing 100 μg/ml ampicillin and 50 μg/ml kanamycin, and plasmid DNA was prepared by alkaline lysis. The plasmids were screened for insertions by digestion with BamHI. Those recombinants containing inserts were grown in L-broth containing ampicillin and kanamycin and tested for the expression of thermophilic DNA polymerase by induction of exponentially growing culture with 1 mM IPTG and assaying the heat-treated extracts for DNA polymerase activity as described above (determination of DNA polymerase activity). A recombinant expressing the DNA polymerase from *Carboxydothermus hydrogenoformans* was obtained. The strain was designated *E.coli* AR96 (DSM No. 11179) and the plasmid pAR4.

We claim:

1. An isolated DNA polymerase comprising SEQ ID NO:8.
2. An isolated DNA sequence encoding the DNA polymerase of claim 1.
3. An isolated DNA sequence comprising SEQ ID NO:7.
4. A vector comprising a DNA sequence which encodes SEQ ID NO:8 comprising a DNA sequence which encodes SEQ ID NO:8.
5. The vector of claim 4 that is pAR4.
6. A host cell comprising the vector of claim 4 or 5.
7. The host cell of claim 6 that is AR96.
8. A vector comprising SEQ ID NO: 7.

* * * * *

SEQUENCE LISTING

<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: amplification primer
<221> NAME/KEY: misc_feature
<222> LOCATION: (3)..(3)
<223> OTHER INFORMATION: any nucleotide
<221> NAME/KEY: misc_feature
<222> LOCATION: (9)..(9)
<223> OTHER INFORMATION: any nucleotide

<400> SEQUENCE: 1
ccnaayytnc araayath                                                    18

<210> SEQ ID NO 2
<211> LENGTH: 15
<212> TYPE: DNA
<213> ORGANISM: Artificial Sequence
<220> FEATURE:
<223> OTHER INFORMATION: amplification primer
<221> NAME/KEY: misc_feature
<222> LOCATION: (10)..(10)

<223> OTHER INFORMATION: any nucleotide

<400> SEQUENCE: 2
ytcrtcrtgn acytg  15

<210> SEQ ID NO 3
<211> LENGTH: 25
<212> TYPE: DNA
<213> ORGANISM: Artificial Sequence
<220> FEATURE:
<223> OTHER INFORMATION: amplification primer

<400> SEQUENCE: 3
gggcgaagac gctatattcc tgagc  25

<210> SEQ ID NO 4
<211> LENGTH: 28
<212> TYPE: DNA
<213> ORGANISM: Artificial Sequence
<220> FEATURE:
<223> OTHER INFORMATION: amplification primer

<400> SEQUENCE: 4
gaagccttaa ttcaatctgg gaataatc  28

<210> SEQ ID NO 5
<211> LENGTH: 36
<212> TYPE: DNA
<213> ORGANISM: Artificial Sequence
<220> FEATURE:
<223> OTHER INFORMATION: amplification primer

<400> SEQUENCE: 5
cgaattcaat ccatgggaaa agtagtcctg gtggat  36

<210> SEQ ID NO 6
<211> LENGTH: 36
<212> TYPE: DNA
<213> ORGANISM: Artificial Sequence
<220> FEATURE:
<223> OTHER INFORMATION: amplification primer

<400> SEQUENCE: 6
cgaattcaag gatccttact tcgcttcata ccagtt  36

<210> SEQ ID NO 7
<211> LENGTH: 2496
<212> TYPE: DNA
<213> ORGANISM: Carboxydothermus hydrogenoformans
<220> FEATURE:
<221> NAME/KEY: CDS
<222> LOCATION: (1)..(2496)

<400> SEQUENCE: 7

| atg | gga | aaa | gta | gtc | ctg | gtg | gat | gga | aat | agt | tta | tta | cat | aga | gcg | 48 |
| Met | Gly | Lys | Val | Val | Leu | Val | Asp | Gly | Asn | Ser | Leu | Leu | His | Arg | Ala | |
| 1 | | | | 5 | | | | | 10 | | | | | 15 | | |

| ttt | ttt | gcc | ctt | ccg | ccc | tta | aaa | act | act | aaa | gga | gag | cct | acc | ggg | 96 |
| Phe | Phe | Ala | Leu | Pro | Pro | Leu | Lys | Thr | Thr | Lys | Gly | Glu | Pro | Thr | Gly | |
| | | | 20 | | | | | 25 | | | | | 30 | | | |

| gcg | gtt | tac | ggg | ttt | tta | acg | atg | ctt | ttt | cgg | gta | ata | aaa | gat | gaa | 144 |
| Ala | Val | Tyr | Gly | Phe | Leu | Thr | Met | Leu | Phe | Arg | Val | Ile | Lys | Asp | Glu | |
| | | 35 | | | | | 40 | | | | | 45 | | | | |

| aaa | ccc | gaa | tat | tta | gcg | gta | gct | ttt | gat | att | agc | cgg | aaa | act | ttt | 192 |
| Lys | Pro | Glu | Tyr | Leu | Ala | Val | Ala | Phe | Asp | Ile | Ser | Arg | Lys | Thr | Phe | |

```
              50                  55                  60
cgt acc gag cag ttt act gca tac aaa ggg cac cgc aaa gaa gcc ccg       240
Arg Thr Glu Gln Phe Thr Ala Tyr Lys Gly His Arg Lys Glu Ala Pro
 65                  70                  75                  80 gat gag ctt gta ccc cag ttt gcc ctg gtg cgg gaa gta tta aag gtt       288
Asp Glu Leu Val Pro Gln Phe Ala Leu Val Arg Glu Val Leu Lys Val
                 85                  90                  95 tta aat gtt ccc tat att gaa ctt gac ggt tat gag gcc gat gat att       336
Leu Asn Val Pro Tyr Ile Glu Leu Asp Gly Tyr Glu Ala Asp Asp Ile
                100                 105                 110 atc ggc cac cta tca agg gct ttt gcg gga caa gga cat gaa gtg gtg       384
Ile Gly His Leu Ser Arg Ala Phe Ala Gly Gln Gly His Glu Val Val
            115                 120                 125 att tat acc gct gac cgg gac atg ctg caa ttg gta gat gaa aaa acg       432
Ile Tyr Thr Ala Asp Arg Asp Met Leu Gln Leu Val Asp Glu Lys Thr
        130                 135                 140 gtg gta tac ctt acc aaa aaa ggc att acc gaa ctg gtt aaa atg gat       480
Val Val Tyr Leu Thr Lys Lys Gly Ile Thr Glu Leu Val Lys Met Asp
145                 150                 155                 160 tta gct gcg att tta gaa aac tac ggc tta aag cct aaa cag ctt gtg       528
Leu Ala Ala Ile Leu Glu Asn Tyr Gly Leu Lys Pro Lys Gln Leu Val
                165                 170                 175 gat gtt aaa gga tta atg gga gat ccc tcg gac aac ata ccc ggg gtt       576
Asp Val Lys Gly Leu Met Gly Asp Pro Ser Asp Asn Ile Pro Gly Val
            180                 185                 190 ccc ggg att ggg gag aaa act gct tta gat tta att aaa act tat ggc       624
Pro Gly Ile Gly Glu Lys Thr Ala Leu Asp Leu Ile Lys Thr Tyr Gly
        195                 200                 205 tca gtg gaa gaa gtt ttg gcc cgt aaa gat gag tta aaa cct aaa tta       672
Ser Val Glu Glu Val Leu Ala Arg Lys Asp Glu Leu Lys Pro Lys Leu
210                 215                 220 aga gaa aag ctt gcc gaa cac gaa aat tta gca aaa ata tcg aaa caa       720
Arg Glu Lys Leu Ala Glu His Glu Asn Leu Ala Lys Ile Ser Lys Gln
225                 230                 235                 240 tta gct aca atc ctg cgg gaa ata ccg tta gaa atc tcc ctg gaa gat       768
Leu Ala Thr Ile Leu Arg Glu Ile Pro Leu Glu Ile Ser Leu Glu Asp
                245                 250                 255 tta aaa gtt aaa gaa cct aat tat gaa gaa gtt gct aaa tta ttt ctt       816
Leu Lys Val Lys Glu Pro Asn Tyr Glu Glu Val Ala Lys Leu Phe Leu
            260                 265                 270 cac ctt gag ttt aaa agc ttt tta aaa gaa ata gaa cca aaa ata aag       864
His Leu Glu Phe Lys Ser Phe Leu Lys Glu Ile Glu Pro Lys Ile Lys
        275                 280                 285 aaa gaa tac cag gaa ggt aaa gat ttg gtg caa gtt gaa act gta gaa       912
Lys Glu Tyr Gln Glu Gly Lys Asp Leu Val Gln Val Glu Thr Val Glu
290                 295                 300 acg gaa gga cag att gca gta gtt ttt agt gat gga ttt tat gtt gat       960
Thr Glu Gly Gln Ile Ala Val Val Phe Ser Asp Gly Phe Tyr Val Asp
305                 310                 315                 320 gac ggg gaa aaa aca aag ttt tac tct tta gac cgg ctg aat gaa ata      1008
Asp Gly Glu Lys Thr Lys Phe Tyr Ser Leu Asp Arg Leu Asn Glu Ile
                325                 330                 335 gag gaa ata ttt agg aat aaa aaa att att acc gac gat gcc aaa gga      1056
Glu Glu Ile Phe Arg Asn Lys Lys Ile Ile Thr Asp Asp Ala Lys Gly
            340                 345                 350 att tat cat gtc tgt tta gaa aaa ggt ctg act ttt ccc gaa gtt tgt      1104
Ile Tyr His Val Cys Leu Glu Lys Gly Leu Thr Phe Pro Glu Val Cys
        355                 360                 365 ttt gat gcg cgg att gca gct tat gtt tta aac ccg gcc gac caa aat      1152
```

-continued

```
Phe Asp Ala Arg Ile Ala Ala Tyr Val Leu Asn Pro Ala Asp Gln Asn
    370                 375                 380 ccc ggc ctc aag ggg ctt tat cta aag tat gac tta ccg gtg tat gaa        1200
Pro Gly Leu Lys Gly Leu Tyr Leu Lys Tyr Asp Leu Pro Val Tyr Glu
385                 390                 395                 400 gat gta tct tta aac att aga ggg ttg ttt tat tta aaa aaa gaa atg        1248
Asp Val Ser Leu Asn Ile Arg Gly Leu Phe Tyr Leu Lys Lys Glu Met
                405                 410                 415 atg aga aaa atc ttt gag cag gag caa gaa agg tta ttt tat gaa ata        1296
Met Arg Lys Ile Phe Glu Gln Glu Gln Glu Arg Leu Phe Tyr Glu Ile
            420                 425                 430 gaa ctt cct tta act cca gtt ctt gct caa atg gag cat acc ggc att        1344
Glu Leu Pro Leu Thr Pro Val Leu Ala Gln Met Glu His Thr Gly Ile
        435                 440                 445 cag gtt gac cgg gaa gct tta aaa gag atg tcg tta gag ctg gga gag        1392
Gln Val Asp Arg Glu Ala Leu Lys Glu Met Ser Leu Glu Leu Gly Glu
    450                 455                 460 caa att gaa gag tta atc cgg gaa att tat gtg ctg gcg ggg gaa gag        1440
Gln Ile Glu Glu Leu Ile Arg Glu Ile Tyr Val Leu Ala Gly Glu Glu
465                 470                 475                 480 ttt aac tta aac tcg ccc agg cag ctg gga gtt att ctt ttt gaa aaa        1488
Phe Asn Leu Asn Ser Pro Arg Gln Leu Gly Val Ile Leu Phe Glu Lys
                485                 490                 495 ctt ggg ctg ccg gta att aaa aag acc aaa acg ggc tac tct acc gat        1536
Leu Gly Leu Pro Val Ile Lys Lys Thr Lys Thr Gly Tyr Ser Thr Asp
            500                 505                 510 gcg gag gtt ttg gaa gag ctc ttg cct ttc cac gaa att ggc atc ggc        1584
Ala Glu Val Leu Glu Glu Leu Leu Pro Phe His Glu Ile Gly Ile Gly
        515                 520                 525 aaa ata ttg aat tac cgg cag ctt atg aag tta aaa tcc act tat act        1632
Lys Ile Leu Asn Tyr Arg Gln Leu Met Lys Leu Lys Ser Thr Tyr Thr
    530                 535                 540 gac tta atg cct tta ata aat gag cgt acc ggt aaa ctt cac act act        1680
Asp Leu Met Pro Leu Ile Asn Glu Arg Thr Gly Lys Leu His Thr Thr
545                 550                 555                 560 ttt aac cag acc ggt act tta acc gga cgc ctg gcg tct tcg gag ccc        1728
Phe Asn Gln Thr Gly Thr Leu Thr Gly Arg Leu Ala Ser Ser Glu Pro
                565                 570                 575 aat ctc caa aat att ccc atc cgg ttg gaa ctc ggt cgg aaa tta cgc        1776
Asn Leu Gln Asn Ile Pro Ile Arg Leu Glu Leu Gly Arg Lys Leu Arg
            580                 585                 590 aag atg ttt ata cct tca ccg ggg tat gat tat att gtt tcg gcg gat        1824
Lys Met Phe Ile Pro Ser Pro Gly Tyr Asp Tyr Ile Val Ser Ala Asp
        595                 600                 605 tat tcc cag att gaa tta agg ctt ctt gcc cat ttt tcc gaa gag ccc        1872
Tyr Ser Gln Ile Glu Leu Arg Leu Leu Ala His Phe Ser Glu Glu Pro
    610                 615                 620 aag ctt att gaa gct tac caa aaa ggg gag gat att cac cgg aaa acg        1920
Lys Leu Ile Glu Ala Tyr Gln Lys Gly Glu Asp Ile His Arg Lys Thr
625                 630                 635                 640 gcc tcc gag gtg ttc ggt gta tct ttg gaa gaa gtt act ccc gag atg        1968
Ala Ser Glu Val Phe Gly Val Ser Leu Glu Glu Val Thr Pro Glu Met
                645                 650                 655 cgc gct cat gcc aag tcg gtg aac ttc ggc att gtt tat ggc att agt        2016
Arg Ala His Ala Lys Ser Val Asn Phe Gly Ile Val Tyr Gly Ile Ser
            660                 665                 670 gat ttt ggt tta ggc aga gac tta aag att ccc cgg gag gtt gcc ggt        2064
Asp Phe Gly Leu Gly Arg Asp Leu Lys Ile Pro Arg Glu Val Ala Gly
        675                 680                 685
```

```
aag tac att aaa aat tat ttt gcc aac tat ccc aaa gtg cgg gag tat    2112
Lys Tyr Ile Lys Asn Tyr Phe Ala Asn Tyr Pro Lys Val Arg Glu Tyr
        690             695                 700 ctc gat gaa ctt gtc cgt acg gca aga gaa aag gga tat gtg acc act    2160
Leu Asp Glu Leu Val Arg Thr Ala Arg Glu Lys Gly Tyr Val Thr Thr
705                 710                 715                 720 tta ttt ggg cga aga cgc tat att cct gag cta tct tca aaa aac cgc    2208
Leu Phe Gly Arg Arg Arg Tyr Ile Pro Glu Leu Ser Ser Lys Asn Arg
                725                 730                 735 acg gtt cag ggt ttt ggc gaa agg acg gcc atg aat act ccc ctt cag    2256
Thr Val Gln Gly Phe Gly Glu Arg Thr Ala Met Asn Thr Pro Leu Gln
            740                 745                 750 ggc tcg gct gcc gat att att aag ctt gca atg att aat gta gaa aaa    2304
Gly Ser Ala Ala Asp Ile Ile Lys Leu Ala Met Ile Asn Val Glu Lys
        755                 760                 765 gaa ctt aaa gcc cgt aag ctt aag tcc cgg ctc ctt ctt tcg gtg cac    2352
Glu Leu Lys Ala Arg Lys Leu Lys Ser Arg Leu Leu Leu Ser Val His
770                 775                 780 gat gag tta gtt tta gaa gtg ccg gcg gaa gag ctg gaa gag gta aaa    2400
Asp Glu Leu Val Leu Glu Val Pro Ala Glu Glu Leu Glu Glu Val Lys
785                 790                 795                 800 gcg ctg gta aaa ggg gtt atg gag tcg gtg gtt gaa ctg aaa gtg cct    2448
Ala Leu Val Lys Gly Val Met Glu Ser Val Val Glu Leu Lys Val Pro
                805                 810                 815 tta atc gct gaa gtt ggt gca ggc aaa aac tgg tat gaa gcg aag taa    2496
Leu Ile Ala Glu Val Gly Ala Gly Lys Asn Trp Tyr Glu Ala Lys
            820                 825                 830

<210> SEQ ID NO 8
<211> LENGTH: 831
<212> TYPE: PRT
<213> ORGANISM: Carboxydothermus hydrogenoformans

<400> SEQUENCE: 8

Met Gly Lys Val Val Leu Val Asp Gly Asn Ser Leu Leu His Arg Ala
1               5                   10                  15

Phe Phe Ala Leu Pro Pro Leu Lys Thr Thr Lys Gly Glu Pro Thr Gly
            20                  25                  30

Ala Val Tyr Gly Phe Leu Thr Met Leu Phe Arg Val Ile Lys Asp Glu
        35                  40                  45

Lys Pro Glu Tyr Leu Ala Val Ala Phe Asp Ile Ser Arg Lys Thr Phe
    50                  55                  60

Arg Thr Glu Gln Phe Thr Ala Tyr Lys Gly His Arg Lys Glu Ala Pro
65                  70                  75                  80

Asp Glu Leu Val Pro Gln Phe Ala Leu Val Arg Glu Val Leu Lys Val
                85                  90                  95

Leu Asn Val Pro Tyr Ile Glu Leu Asp Gly Tyr Glu Ala Asp Asp Ile
            100                 105                 110

Ile Gly His Leu Ser Arg Ala Phe Ala Gly Gln Gly His Glu Val Val
        115                 120                 125

Ile Tyr Thr Ala Asp Arg Asp Met Leu Gln Leu Val Asp Glu Lys Thr
    130                 135                 140

Val Val Tyr Leu Thr Lys Lys Gly Ile Thr Glu Leu Val Lys Met Asp
145                 150                 155                 160

Leu Ala Ala Ile Leu Glu Asn Tyr Gly Leu Lys Pro Lys Gln Leu Val
                165                 170                 175

Asp Val Lys Gly Leu Met Gly Asp Pro Ser Asp Asn Ile Pro Gly Val
            180                 185                 190
```

```
Pro Gly Ile Gly Glu Lys Thr Ala Leu Asp Leu Ile Lys Thr Tyr Gly
        195                 200                 205
Ser Val Glu Glu Val Leu Ala Arg Lys Asp Glu Leu Lys Pro Lys Leu
        210                 215                 220
Arg Glu Lys Leu Ala Glu His Glu Asn Leu Ala Lys Ile Ser Lys Gln
225                 230                 235                 240
Leu Ala Thr Ile Leu Arg Glu Ile Pro Leu Glu Ile Ser Leu Glu Asp
                245                 250                 255
Leu Lys Val Lys Glu Pro Asn Tyr Glu Glu Val Ala Lys Leu Phe Leu
            260                 265                 270
His Leu Glu Phe Lys Ser Phe Leu Lys Glu Ile Glu Pro Lys Ile Lys
        275                 280                 285
Lys Glu Tyr Gln Glu Gly Lys Asp Leu Val Gln Val Glu Thr Val Glu
        290                 295                 300
Thr Glu Gly Gln Ile Ala Val Val Phe Ser Asp Gly Phe Tyr Val Asp
305                 310                 315                 320
Asp Gly Glu Lys Thr Lys Phe Tyr Ser Leu Asp Arg Leu Asn Glu Ile
                325                 330                 335
Glu Glu Ile Phe Arg Asn Lys Ile Ile Thr Asp Asp Ala Lys Gly
            340                 345                 350
Ile Tyr His Val Cys Leu Glu Lys Gly Leu Thr Phe Pro Glu Val Cys
        355                 360                 365
Phe Asp Ala Arg Ile Ala Ala Tyr Val Leu Asn Pro Ala Asp Gln Asn
        370                 375                 380
Pro Gly Leu Lys Gly Leu Tyr Leu Lys Tyr Asp Leu Pro Val Tyr Glu
385                 390                 395                 400
Asp Val Ser Leu Asn Ile Arg Gly Leu Phe Tyr Leu Lys Lys Glu Met
                405                 410                 415
Met Arg Lys Ile Phe Glu Gln Glu Gln Glu Arg Leu Phe Tyr Glu Ile
            420                 425                 430
Glu Leu Pro Leu Thr Pro Val Leu Ala Gln Met Glu His Thr Gly Ile
        435                 440                 445
Gln Val Asp Arg Glu Ala Leu Lys Glu Met Ser Leu Glu Leu Gly Glu
        450                 455                 460
Gln Ile Glu Glu Leu Ile Arg Glu Ile Tyr Val Leu Ala Gly Glu Glu
465                 470                 475                 480
Phe Asn Leu Asn Ser Pro Arg Gln Leu Gly Val Ile Leu Phe Glu Lys
                485                 490                 495
Leu Gly Leu Pro Val Ile Lys Lys Thr Lys Thr Gly Tyr Ser Thr Asp
            500                 505                 510
Ala Glu Val Leu Glu Glu Leu Leu Pro Phe His Glu Ile Gly Ile Gly
        515                 520                 525
Lys Ile Leu Asn Tyr Arg Gln Leu Met Lys Leu Lys Ser Thr Tyr Thr
        530                 535                 540
Asp Leu Met Pro Leu Ile Asn Glu Arg Thr Gly Lys Leu His Thr Thr
545                 550                 555                 560
Phe Asn Gln Thr Gly Thr Leu Thr Gly Arg Leu Ala Ser Ser Glu Pro
                565                 570                 575
Asn Leu Gln Asn Ile Pro Ile Arg Leu Glu Leu Gly Arg Lys Leu Arg
            580                 585                 590
Lys Met Phe Ile Pro Ser Pro Gly Tyr Asp Tyr Ile Val Ser Ala Asp
        595                 600                 605
```

```
Tyr Ser Gln Ile Glu Leu Arg Leu Leu Ala His Phe Ser Glu Glu Pro
    610             615                 620
Lys Leu Ile Glu Ala Tyr Gln Lys Gly Glu Asp Ile His Arg Lys Thr
625                 630                 635                 640
Ala Ser Glu Val Phe Gly Val Ser Leu Glu Glu Val Thr Pro Glu Met
                645                 650                 655
Arg Ala His Ala Lys Ser Val Asn Phe Gly Ile Val Tyr Gly Ile Ser
                660                 665                 670
Asp Phe Gly Leu Gly Arg Asp Leu Lys Ile Pro Arg Glu Val Ala Gly
            675                 680                 685
Lys Tyr Ile Lys Asn Tyr Phe Ala Asn Tyr Pro Lys Val Arg Glu Tyr
    690                 695                 700
Leu Asp Glu Leu Val Arg Thr Ala Arg Glu Lys Gly Tyr Val Thr Thr
705                 710                 715                 720
Leu Phe Gly Arg Arg Arg Tyr Ile Pro Glu Leu Ser Ser Lys Asn Arg
                725                 730                 735
Thr Val Gln Gly Phe Gly Glu Arg Thr Ala Met Asn Thr Pro Leu Gln
            740                 745                 750
Gly Ser Ala Ala Asp Ile Ile Lys Leu Ala Met Ile Asn Val Glu Lys
            755                 760                 765
Glu Leu Lys Ala Arg Lys Leu Lys Ser Arg Leu Leu Leu Ser Val His
    770                 775                 780
Asp Glu Leu Val Leu Glu Val Pro Ala Glu Glu Leu Glu Glu Val Lys
785                 790                 795                 800
Ala Leu Val Lys Gly Val Met Glu Ser Val Val Glu Leu Lys Val Pro
                805                 810                 815
Leu Ile Ala Glu Val Gly Ala Gly Lys Asn Trp Tyr Glu Ala Lys
                820                 825                 830

<210> SEQ ID NO 9
<211> LENGTH: 22
<212> TYPE: DNA
<213> ORGANISM: Artificial Sequence
<220> FEATURE:
<223> OTHER INFORMATION: amplification primer

<400> SEQUENCE: 9
gcatggatcc cactgcccag gg                                         22
```